(12) United States Patent
Bai

(10) Patent No.: US 10,048,254 B2
(45) Date of Patent: Aug. 14, 2018

(54) CYCLIC-DI-AMP SPECIFIC DETECTION

(71) Applicant: ALBANY MEDICAL COLLEGE, Albany, NY (US)

(72) Inventor: Guangchun Bai, Delmar, NY (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 212 days.

(21) Appl. No.: 14/896,117

(22) PCT Filed: Jun. 3, 2014

(86) PCT No.: PCT/US2014/040726
§ 371 (c)(1),
(2) Date: Dec. 4, 2015

(87) PCT Pub. No.: WO2014/197490
PCT Pub. Date: Dec. 11, 2014

(65) Prior Publication Data
US 2016/0123966 A1 May 5, 2016

Related U.S. Application Data

(60) Provisional application No. 61/830,884, filed on Jun. 4, 2013.

(51) Int. Cl.
G01N 33/53 (2006.01)
G01N 33/566 (2006.01)

(52) U.S. Cl.
CPC ....... *G01N 33/5308* (2013.01); *G01N 33/566* (2013.01); *G01N 2333/4703* (2013.01)

(58) Field of Classification Search
None
See application file for complete search history.

(56) References Cited

U.S. PATENT DOCUMENTS 6,800,744 B1  10/2004  Doucette-Stamm et al.

FOREIGN PATENT DOCUMENTS

WO  99/41609 A1  8/1999
WO  02/077021 A2  10/2002

OTHER PUBLICATIONS

Diamandis et al., Immnoassay, Academic Press, Chapter 11, the Avidin-Biotin System, pp. 237-255, 1996. (Year: 1996).*
Bai, et al. "Cyclic Di-AMP Impairs Potassium Uptake Mediated by a Cyclic Di-AMP Binding Protein in *Streptococcus pneumoniae*", *Journal of Bacteriology*, vol. 196(3), pp. 614-623 (2013).
Burdette et al. "STING is a Direct Innate Immune Sensor of Cyclic Di-GMP", *Nature*, vol. 478, pp. 515-519 (2011).
Underwood et al. "Detection of Cyclic Di-AMP Using a Competitive ELISA With a Unique Pneumococcal Cyclic Di-AMP Binding Protein", *Journal of Microbiological Methods*, vol. 107, pp. 58-62 (2014).
Parvatiyar et al. "DDX41 Recognizes Bacterial Secondary Messengers Cyclic Di-GMP and Cyclic Di-AMP to Activate a Type I Interferon Immune Response", *Nature Immunology*, vol. 13, pp. 1155-1161 (2012).

* cited by examiner

*Primary Examiner* — Gary Counts
(74) *Attorney, Agent, or Firm* — Helsin Rothenberg Farley and Mesiti, PC; Kathy Smith Dias

(57) ABSTRACT

The present disclosure provides a simple yet fast, cost effective, reliable method for the detection and quantification of cyclic-di-adenosine monophosphate (c-di-AMP) by measuring c-di-AMP binding to a c-di-AMP-binding protein (CabP). A sample is contacted with CabP in the presence of biotin-labeled c-di-AMP. Once binding has reached equilibrium, unbound c-di-AMP is removed and the CabP-bound c-di-AMP is contacted with an enzyme-conjugated biotin-binding protein and a chromogenic substrate to generate a detectable signal. The signal generated correlates to the amount of unlabeled c-di-AMP in the sample.

7 Claims, 10 Drawing Sheets

SEQUENCE LISTING

```
<160> NUMBER OF SEQ ID NOS: 8

<210> SEQ ID NO 1
<211> LENGTH: 221
<212> TYPE: PRT
<213> ORGANISM: Streptococcus pneumoniae

<400> SEQUENCE: 1

Met Ser Asp Arg Thr Ile Gly Ile Leu Gly Leu Gly Ile Phe Gly Ser
1               5                   10                  15

Ser Val Leu Ala Ala Leu Ala Lys Gln Asp Met Asn Ile Ile Ala Ile
                20                  25                  30

Asp Asp His Ala Glu Arg Ile Asn Gln Phe Glu Pro Val Leu Ala Arg
            35                  40                  45

Gly Val Ile Gly Asp Ile Thr Asp Glu Glu Leu Leu Arg Ser Ala Gly
        50                  55                  60

Ile Asp Thr Cys Asp Thr Val Val Ala Thr Gly Glu Asn Leu Glu
65                  70                  75                  80

Ser Ser Val Leu Ala Val Met His Cys Lys Ser Leu Gly Val Pro Thr
                85                  90                  95

Val Ile Ala Lys Val Lys Ser Gln Thr Ala Lys Lys Val Leu Glu Lys
                100                 105                 110

Ile Gly Ala Asp Ser Val Ile Ser Pro Glu Tyr Glu Met Gly Gln Ser
            115                 120                 125

Leu Ala Gln Thr Ile Leu Phe His Asn Ser Val Asp Val Phe Gln Leu
```

```
                130                 135                 140
Asp Lys Asn Val Ser Ile Val Glu Met Lys Ile Pro Gln Ser Trp Ala
145                 150                 155                 160

Gly Gln Ser Leu Ser Lys Leu Asp Leu Arg Gly Lys Tyr Asn Leu Asn
                165                 170                 175

Ile Leu Gly Phe Arg Glu Gln Glu Asn Ser Pro Leu Asp Val Glu Phe
            180                 185                 190

Gly Pro Asp Asp Leu Leu Lys Ala Asp Thr Tyr Ile Leu Ala Val Ile
            195                 200                 205

Asn Asn Gln Tyr Leu Asp Thr Leu Val Ala Leu Asn Ser
            210                 215                 220

<210> SEQ ID NO 2
<211> LENGTH: 5972
<212> TYPE: DNA
<213> ORGANISM: Artificial Sequence
<220> FEATURE:
<223> OTHER INFORMATION: recombinant plasmid

<400> SEQUENCE: 2
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttac     180
gaattcaatg ctactagggt atccaaatac tggttgttga tgactgccaa aatataggta     240
tctgctttca agaggtcatc tggtccaaat tcaacatcca atggggaatt ttcctgctct     300
cggaaaccca aaatattcag attgtatttg ccacggaggt ctaatttact cagactttga     360
cctgcccaag actgaggaat ttcatctcc acgatagaca catttttatc caactgaaag     420
acatcaacac tattatggaa aagaatggtc tgtgctagag actgccccat ttcatactct     480
ggcgagataa ccgagtcagc tccaatcttt tctagcactt tcttagcggt ctgacttttg     540
accttagcaa taacagtcgg tacccccaaa ctcttacagt gcataaccgc aagcacactc     600
gactccagat tttcacctgt cgcgactaca acggtatcgc aggtatcaat ccctgctgat     660
ctcaataatt cttcatctgt gatgtcacca atcactccac gcgccaaaac tggctcaaac     720
tgattgatgc gctctgcgtg gtcatcaata gcgataatat tcatatcctg cttggctagg     780
gcagctagga cactgctccc aaaaattccc aagcccaaaa ttccaatcgt acgatctgac     840
atatggctgc cgcgcggcac caggccgctg ctgtgatgat gatgatgatg ctgctgcccc    900
atggtatatc tccttcttaa agttaaacaa aattatttct agaggggaat tgttatccgc     960
tcacaattcc cctatagtga gtcgtattaa tttcgcggga tcgagatctc gatcctctac    1020 gccgacgca tcgtggccgg catcaccggc gccacaggtg cggttgctgg cgcctatatc    1080
gccgacatca ccgatgggga agatcgggct cgccacttcg gctcatgag cgcttgtttc    1140 ggcgtgggta tggtggcagg ccccgtggcc ggggactgt tgggcgccat ctccttgcat    1200
gcaccattcc ttgcggcggc ggtgctcaac ggcctcaacc tactactggg ctgcttccta    1260
atgcaggagt cgcataaggg agagcgtcga tcccggac accatcgaat ggcgcaaaac    1320
ctttcgcggt atggcatgat agcgcccgga agagagtcaa ttcagggtgg tgaatgtgaa    1380
accagtaacg ttatacgatg tcgcagagta tgccggtgtc tcttatcaga ccgtttcccg    1440
cgtggtgaac caggccagcc acgtttctgc gaaaacgcgg gaaaaagtgg aagcggcgat    1500
ggcggagctg aattacattc ccaaccgcgt ggcacaacaa ctggcgggca aacagtcgtt    1560
```

```
gctgattggc gttgccacct ccagtctggc cctgcacgcg ccgtcgcaaa ttgtcgcggc    1620
gattaaatct cgcgccgatc aactgggtgc cagcgtggtg gtgtcgatgg tagaacgaag    1680
cggcgtcgaa gcctgtaaag cggcggtgca caatcttctc gcgcaacgcg tcagtgggct    1740
gatcattaac tatccgctgg atgaccagga tgccattgct gtggaagctg cctgcactaa    1800
tgttccggcg ttatttcttg atgtctctga ccagacaccc atcaacagta ttattttctc    1860
ccatgaagac ggtacgcgac tgggcgtgga gcatctggtc gcattgggtc accagcaaat    1920
cgcgctgtta gcgggcccat taagttctgt ctcggcgcgt ctgcgtctgg ctggctggca    1980
taaatatctc actcgcaatc aaattcagcc gatagcggaa cgggaaggcg actggagtgc    2040
catgtccggt tttcaacaaa ccatgcaaat gctgaatgag ggcatcgttc ccactgcgat    2100
gctggttgcc aacgatcaga tggcgctggg cgcaatgcgc gccattaccg agtccgggct    2160
gcgcgttggt gcggatatct cggtagtggg atacgacgat accgaagaca gctcatgtta    2220
tatcccgccg ttaaccacca tcaaacagga ttttcgcctg ctggggcaaa ccagcgtgga    2280
ccgcttgctg caactctctc agggccaggc ggtgaagggc aatcagctgt tgcccgtctc    2340
actggtgaaa agaaaaacca ccctggcgcc caatacgcaa accgcctctc cccgcgcgtt    2400
ggccgattca ttaatgcagc tggcacgaca ggtttcccga ctggaaagcg ggcagtgagc    2460
gcaacgcaat taatgtaagt tagctcactc attaggcacc gggatctcga ccgatgccct    2520
tgagagcctt caacccagtc agctccttcc ggtgggcgcg gggcatgact atcgtcgccg    2580
cacttatgac tgtcttcttt atcatgcaac tcgtaggaca ggtgccggca gcgctctggg    2640
tcattttcgg cgaggaccgc tttcgctgga gcgcgacgat gatcggcctg tcgcttgcgg    2700
tattcggaat cttgcacgcc ctcgctcaag ccttcgtcac tggtcccgcc accaaacgtt    2760
tcggcgagaa gcaggccatt atcgccgcca tggcggcccc acgggtgcgc atgatcgtgc    2820
tcctgtcgtt gaggacccgg ctaggctggc ggggttgcct tactggttag cagaatgaat    2880
caccgatacg cgagcgaacg tgaagcgact gctgctgcaa aacgtctgcg acctgagcaa    2940
caacatgaat ggtcttcggt ttccgtgttt cgtaaagtct ggaaacgcgg aagtcagcgc    3000
cctgcaccat tatgttccgg atctgcatcg caggatgctg ctggctaccc tgtggaacac    3060
ctacatctgt attaacgaag cgctggcatt gaccctgagt gatttttctc tggtcccgcc    3120
gcatccatac cgccagttgt ttaccctcac aacgttccag taaccgggca tgttcatcat    3180
cagtaacccg tatcgtgagc atcctctctc gtttcatcgg tatcattacc cccatgaaca    3240
gaaatccccc ttacacggag gcatcagtga ccaaacagga aaaaaccgcc cttaacatgg    3300
cccgctttat cagaagccag acattaacgc ttctggagaa actcaacgag ctggacgcgg    3360
atgaacaggc agacatctgt gaatcgcttc acgaccacgc tgatgagctt taccgcagct    3420
gcctcgcgcg tttcggtgat gacggtgaaa acctctgaca catgcagctc ccggagacgg    3480
tcacagcttg tctgtaagcg gatgccggga gcagacaagc ccgtcagggc gcgtcagcgg    3540
gtgttggcgg gtgtcggggc gcagccatga cccagtcacg tagcgatagc ggagtgtata    3600
ctggcttaac tatgcggcat cagagcagat tgtactgaga gtgcaccata tatgcggtgt    3660
gaaataccgc acagatgcgt aaggagaaaa taccgcatca ggcgctcttc cgcttcctcg    3720
ctcactgact cgctgcgctc ggtcgttcgg ctgcggcgag cggtatcagc tcactcaaag    3780
gcggtaatac ggttatccac agaatcaggg gataacgcag gaagaacat gtgagcaaaa    3840 ggccagcaaa aggccaggaa ccgtaaaaag gccgcgttgc tggcgttttt ccataggctc    3900
cgcccccctg acgagcatca aaaaatcga cgctcaagtc agaggtggcg aaacccgaca    3960
```

-continued

```
ggactataaa gataccaggc gtttcccct ggaagctccc tcgtgcgctc tcctgttccg      4020
accctgccgc ttaccggata cctgtccgcc tttctccctt cgggaagcgt ggcgctttct      4080
catagctcac gctgtaggta tctcagttcg gtgtaggtcg ttcgctccaa gctgggctgt      4140
gtgcacgaac ccccgttca gcccgaccgc tgcgccttat ccggtaacta tcgtcttgag      4200
tccaacccgg taagacacga cttatcgcca ctggcagcag ccactggtaa caggattagc      4260
agagcgaggt atgtaggcgg tgctacagag ttcttgaagt ggtggcctaa ctacggctac      4320
actagaagga cagtatttgg tatctgcgct ctgctgaagc cagttacctt cggaaaaaga      4380
gttggtagct cttgatccgg caaacaaacc accgctggta gcggtggttt ttttgtttgc      4440
aagcagcaga ttacgcgcag aaaaaaagga tctcaagaag atcctttgat cttttctacg      4500
gggtctgacg ctcagtggaa cgaaaactca cgttaaggga ttttggtcat gaacaataaa      4560
actgtctgct tacataaaca gtaatacaag gggtgttatg agccatattc aacgggaaac      4620
gtcttgctct aggccgcgat taaattccaa catggatgct gatttatatg ggtataaatg      4680
ggctcgcgat aatgtcgggc aatcaggtgc gacaatctat cgattgtatg ggaagcccga      4740
tgcgccagag ttgtttctga acatggcaa aggtagcgtt gccaatgatg ttacagatga      4800
gatggtcaga ctaaactggc tgacggaatt tatgcctctt ccgaccatca agcattttat      4860
ccgtactcct gatgatgcat ggttactcac cactgcgatc cccgggaaaa cagcattcca      4920
ggtattagaa gaatatcctg attcaggtga aaatattgtt gatgcgctgg cagtgttcct      4980
gcgccggttg cattcgattc ctgtttgtaa ttgtcctttt aacagcgatc gcgtatttcg      5040
tctcgctcag gcgcaatcac gaatgaataa cggtttggtt gatgcgagtg attttgatga      5100
cgagcgtaat ggctggcctg ttgaacaagt ctggaaagaa atgcataaac ttttgccatt      5160
ctcaccggat tcagtcgtca ctcatggtga tttctcactt gataaccta ttttttgacga      5220 ggggaaatta ataggttgta ttgatgttgg acgagtcgga atcgcagacc gataccagga      5280
tcttgccatc ctatggaact gcctcggtga gttttctcct tcattacaga aacggctttt      5340
tcaaaaatat ggtattgata atcctgatat gaataaattg cagtttcatt tgatgctcga      5400
tgagtttttc taagaattaa ttcatgagcg gatacatatt tgaatgtatt tagaaaaata      5460
aacaaatagg ggttccgcgc acatttcccc gaaaagtgcc acctgaaatt gtaaacgtta      5520
atattttgtt aaaattcgcg ttaaattttt gttaaatcag ctcattttt aaccaatagg      5580 ccgaaatcgg caaaatccct tataaatcaa agaatagac cgagataggg ttgagtgttg      5640
ttccagtttg gaacaagagt ccactattaa agaacgtgga ctccaacgtc aaagggcgaa      5700
aaaccgtcta tcagggcgat ggcccactac gtgaaccatc accctaatca agttttttgg      5760
ggtcgaggtg ccgtaaagca ctaaatcgga accctaaagg gagccccga tttagagctt      5820 gacggggaaa gccggcgaac gtggcgagaa aggaagggaa gaaagcgaaa ggagcgggcg      5880
ctagggcgct ggcaagtgta gcggtcacgc tgcgcgtaac caccacaccc gccgcgctta      5940
atgcgccgct acagggcgcg tcccattcgc ca                                   5972
```

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3

```
tttcatatgt cagatcgtac gattgg                                              26

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
tttaagctta cgaattcaat gctac                                               25

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
tttcatatga gcagtgtcct agctgccc                                            28

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
tttaagctta ctgccccatt tcatactctg g                                        31

<210> SEQ ID NO 7
<211> LENGTH: 241
<212> TYPE: PRT
<213> ORGANISM: Artificial Sequence
<220> FEATURE:
<223> OTHER INFORMATION: modified c-di-AMP binding protein

<400> SEQUENCE: 7
```

Met Gly Ser Ser His His His His His His Ser Ser Gly Leu Val Pro
1               5                   10                  15

Arg Gly Ser His Met Ser Asp Arg Thr Ile Gly Ile Leu Gly Leu Gly
            20                  25                  30

Ile Phe Gly Ser Ser Val Leu Ala Ala Leu Ala Lys Gln Asp Met Asn
        35                  40                  45

Ile Ile Ala Ile Asp Asp His Ala Glu Arg Ile Asn Gln Phe Glu Pro
    50                  55                  60

Val Leu Ala Arg Gly Val Ile Gly Asp Ile Thr Asp Glu Glu Leu Leu
65                  70                  75                  80

Arg Ser Ala Gly Ile Asp Thr Cys Asp Thr Val Val Ala Thr Gly
                85                  90                  95

Glu Asn Leu Glu Ser Ser Val Leu Ala Val Met His Cys Lys Ser Leu
            100                 105                 110

Gly Val Pro Thr Val Ile Ala Lys Val Lys Ser Gln Thr Ala Lys Lys
        115                 120                 125

Val Leu Glu Lys Ile Gly Ala Asp Ser Val Ile Ser Pro Glu Tyr Glu
    130                 135                 140

Met Gly Gln Ser Leu Ala Gln Thr Ile Leu Phe His Asn Ser Val Asp
145                 150                 155                 160

Val Phe Gln Leu Asp Lys Asn Val Ser Ile Val Glu Met Lys Ile Pro

-continued

```
                         165                 170                 175
Gln Ser Trp Ala Gly Gln Ser Leu Ser Lys Leu Asp Leu Arg Gly Lys
            180                 185                 190

Tyr Asn Leu Asn Ile Leu Gly Phe Arg Glu Gln Glu Asn Ser Pro Leu
        195                 200                 205

Asp Val Glu Phe Gly Pro Asp Asp Leu Leu Lys Ala Asp Thr Tyr Ile
    210                 215                 220

Leu Ala Val Ile Asn Asn Gln Tyr Leu Asp Thr Leu Val Ala Leu Asn
225                 230                 235                 240

Ser
```

<210> SEQ ID NO 8
<211> LENGTH: 666
<212> TYPE: DNA
<213> ORGANISM: Streptococcus pneumoniae

<400> SEQUENCE: 8

```
atgtcagatc gtacgattgg aattttgggc ttgggaattt ttgggagcag tgtcctagct      60
gccctagcca agcaggatat gaatattatc gctattgatg accacgcaga gcgcatcaat     120
cagtttgagc cagttttggc gcgtggagtg attggtgaca tcacagatga agaattattg     180
agatcagcag ggattgatac ctgcgatacc gttgtagtcg cgacaggtga aaatctggag     240
tcgagtgtgc ttgcggttat gcactgtaag agtttggggg taccgactgt tattgctaag     300
gtcaaaagtc agaccgctaa gaaagtgcta gaaaagattg gagctgactc ggttatctcg     360
ccagagtatg aaatggggca gtctctagca cagaccattc ttttccataa tagtgttgat     420
gtctttcagt tggataaaaa tgtgtctatc gtggagatga aaattcctca gtcttgggca     480
ggtcaaagtc tgagtaaatt agacctccgt ggcaaataca atctgaatat tttgggtttc     540
cgagagcagg aaaattcccc attggatgtt gaatttggac cagatgacct cttgaaagca     600
gatacctata ttttggcagt catcaacaac cagtatttgg atacccctagt agcattgaat     660 tcgtaa                                                                666
```

CYCLIC-DI-AMP SPECIFIC DETECTION

CROSS REFERENCE TO RELATED APPLICATIONS

This application is a National stage filing under section 371 of International Application No. PCT/US2014/040726, filed on Jun. 3, 2014 and published as WO 2014/197490 on Dec. 11, 2014, which claims priority to U.S. provisional application 61/830,884 filed on Jun. 4, 2013. The entire contents of each of said applications are hereby incorporated herein by reference.

STATEMENT REGARDING FEDERALLY SPONSORED RESEARCH OR DEVELOPMENT

This invention was made with U.S. Government support under grant number R01 DC006917 from the National Institutes of Health. The government has certain rights in the invention.

TECHNICAL FIELD

The present invention relates generally to cyclic di-adenosine monophosphate (c-di-AMP). More particularly, the present invention relates to the role of c-di-AMP as a signaling molecule and a method for the detection and quantification of c-di-AMP.

SEQUENCE LISTING

This application contains a Sequence Listing, created on May 15, 2013; the file, in ASCII format, is designated 0410.051P_Sequence Listing_ST25.txt and is 13.6 kilobytes in size. The sequence listing file is hereby incorporated by reference in its entirety into the application.

BACKGROUND OF THE INVENTION

Over the past few decades, cyclic adenosine monophosphate (cAMP), cyclic guanosine monophosphate (cGMP) and cyclic di-guanosine monophosphate (c-di-GMP) have been well studied. These signaling molecules play important biological roles in prokaryotes and their eukaryotic hosts (Gomelsky, 2011, Kalia et al., 2012). In contrast, cyclic di-adenosine monophosphate (c-di-AMP) was recognized only recently as a potential new second messenger in a structural study of DisA by Karl-Peter Hopfner's group in 2008 (Witte et al., 2008). Similar to the paradigms to the other cyclic nucleotides, synthesis, degradation, and secretion of c-di-AMP have been reported in various bacteria, which opens up a new field of research addressing the molecular basis of c-di-AMP network.

Cyclic di-adenosine monophosphate (c-di-AMP) is synthesized from ATP catalyzed by diadenylate cyclase (DAC) and cleaved to pApA or AMP by phosphodiesterase. In bacteria, c-di-AMP levels are precisely maintained; both absence and over-production of c-di-AMP have been shown to be detrimental to several bacteria. The biological roles of c-di-AMP include peptidoglycan homeostasis, resistance to antibiotics and stress conditions, repair of DNA damage and sporulation, and regulation of biofilm formation. c-di-AMP effector proteins have been identified in both prokaryotic and eukaryotic cells. Additionally, c-di-AMP secreted by bacteria induces a type I interferon response in host cells. Therefore, this molecule plays an essential role in bacterial physiology and pathogenesis.

However, the study of c-di-AMP is largely limited due to the lack of a simple but sensitive method for detection. Presently, the detection method commonly used is a liquid chromatography-mass spectrometry (LC-MS)-based analysis, which is relatively complicated.

The tremendous current interest in the biological role of c-di-AMP dictates the need for a sensitive, accurate, and readily performed procedure for estimation of its cellular levels. The methods currently available do not have the extreme sensitivity required by the low tissue levels of the compound, or else they are laborious to perform, or both.

Thus, a need exists for a fast, cost effective, reliable method for the measurement of c-di-AMP.

SUMMARY OF THE INVENTION

The present disclosure relates to materials and methods for the detection and quantification of c-di-AMP.

In one aspect, the invention relates to a method for the detection and/or quantification of c-di-AMP in a sample thought to contain c-di-AMP, comprising: contacting the sample with a c-di-AMP binding protein (CabP) in the presence of biotin-labeled c-di-AMP for a time sufficient for the binding of labeled and unlabeled c-di-AMP to CabP to form c-di-AMP/CabP complexes to come to equilibrium; removing unbound c-di-AMP; contacting the CabP-bound c-di-AMP with an enzyme-conjugated biotin-binding protein that binds the biotin-labeled c-di-AMP bound to the CabP; (c) contacting the enzyme-conjugated biotinylated c-di-AMP with a chromogenic substrate for the enzyme for a time sufficient for oxidation of the substrate to yield a detectable signal; and measuring the detectable signal, where the signal generated in the enzyme/substrate reaction inversely correlates to the amount of unlabeled c-di-AMP in the sample.

In a related aspect, the invention relates to the use of a CabP to detect and quantify c-di-AMP. In one embodiment, the CabP has the amino acid sequence of SEQ ID NO: 1; in one embodiment, the CabP has the sequence of SEQ ID NO: 7

In yet another related aspect, the invention relates to the use of a nucleic acid and/or nucleic acid constructs that encode a CabP having the amino acid sequence of SEQ ID NO: 1 or SEQ ID NO: 7.

Nucleic acid constructs include vectors containing a nucleic acid that encodes a CabP. These vectors are plasmids, viral vectors, phage DNA or other DNA molecules that are able to replicate in a host cell. These vectors may have a selectable marker and any necessary expression control sequences. Such control sequences include, for example, promoters that allow for expression of an ORF in nucleotide sequences operably linked to these promoters.

The vectors may also have multiple cloning sites (MCS) located 3',5', or 3' and 5' of a His-tag coding sequence for expression of 3' or 5' histidine tag-modified polypeptides.

Other embodiments of the invention include recombinant cells containing a vector comprising a CabP coding sequence. The cells can be prokaryotic or eukaryotic, for example, yeast cells, bacterial cells, plant cells and animal cells.

In another related aspect, the invention relates to a kit comprising a CabP comprising the amino acid sequence of SEQ ID NO: 1. Optionally, the kit further comprises: biotin-labeled c-di-AMP; enzyme-conjugated biotin-binding protein; and a chromogenic or fluorogenic substrate for the enzyme. In one embodiment, the kit of the invention contains purified CabP comprising the amino acid sequence of SEQ ID NO: 1. In one embodiment, the enzyme-conjugated biotin-binding protein is horseradish peroxidase (HRP)-streptavidin.

DETAILED DESCRIPTION OF THE INVENTION

Figure 1:
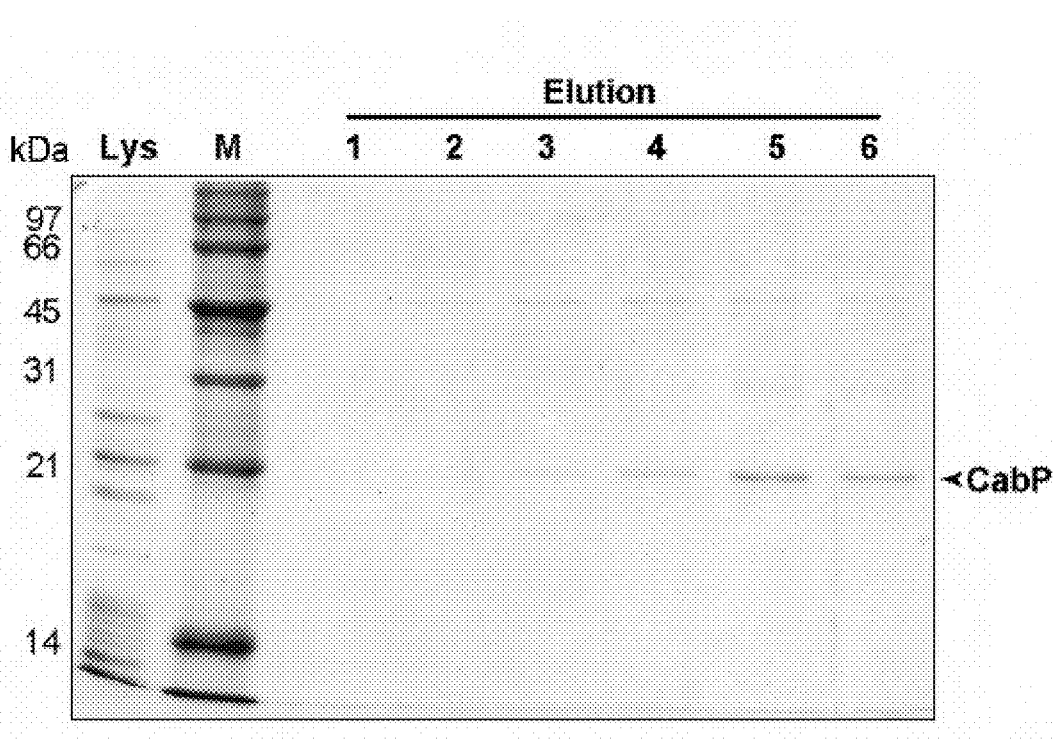
FIG. 1 Purification of c-di-AMP binding protein in *S. pneumoniae* by affinity chromatography using 2'-AHC-c-di-AMP agarose column. The eluted samples were determined by SDS-PAGE, stained with Coomassie Bright Blue, and identified by mass spectrometry (MS). Lys indicates a sample from bacterial lysates that is loaded in the column; M, molecular weight marker (BioRad).

All publications, patents and other references cited herein are incorporated by reference in their entirety into the present disclosure.

In practicing the present invention, many conventional techniques in molecular biology, are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988). The contents of these references and other references containing standard protocols, widely known to and relied upon by those of skill in the art, including manufacturers' instructions are hereby incorporated by reference as part of the present disclosure.

A "histidine tag" (His-tag), as that term is known in the art, refers to a sequence of three or more consecutive histidine amino acid residues. The number of histidine residues in the tag may vary. Generally, 3 to 12 or more residues can be included. In some embodiments, 5 to 10 can be used; or 6 to 8 histidine residues will be encoded. The His-tag may be part of a larger amino acid sequence added to either the N- or C-terminal of the protein of interest.

The term "operably linked" as used herein, means a functional linkage between the expression control sequence and the coding sequence to which it is linked. The operable linkage permits the expression control sequence to control expression of the coding sequence. Expression control sequences can include a promoter, a transcriptional activator binding sequence, an enhancer sequence or any other regulatory or non-regulatory sequence that may be required for transcription and translation of the coding sequence to which the expression control sequence is linked.

In one embodiment, the invention provides for the translation of a histidine tag as part of the CabP, such as the CabP having the amino acid sequence of SEQ ID NO: 7.

The present disclosure provides a method for the detection of c-di-AMP based on the specific binding of c-di-AMP to a binding protein (CabP). The method, a competition binding assay, has a number of advantages over the conventional HPLC-based method. The assay is about 10-100-fold more sensitive than HPLC, enabling detection of c-di-AMP at levels in the nM range. Additionally, the disclosed assay is less costly than LC-MS-based methods and does not require an expensive instrument for processing of samples. Furthermore, less sample is needed and samples are easier to prepare; also, processing time is less.

Detection of c-Di-AMP Using CabP

The present invention provides a simple, rapid and reliable method compared to traditional LC-MS-based methods for measuring c-di-AMP with a sensitivity of about 1-200 nM. The assay is based on the binding of c-di-AMP to a c-di-AMP-binding protein, CabP.

Competitive binding assays are well known in the art and rely on the ability of a labeled ligand to compete with unlabeled ligand in the test sample for binding with a limited amount of binding agent (e.g. antibody, receptor, transport protein). In the present method, the amount of c-di-AMP in the test sample is inversely proportional to the amount of standard (labeled c-di-AMP) that becomes bound to CabP protein.

c-Di-AMP Enzyme-Linked Immunosorbent Assay

Figure 4:
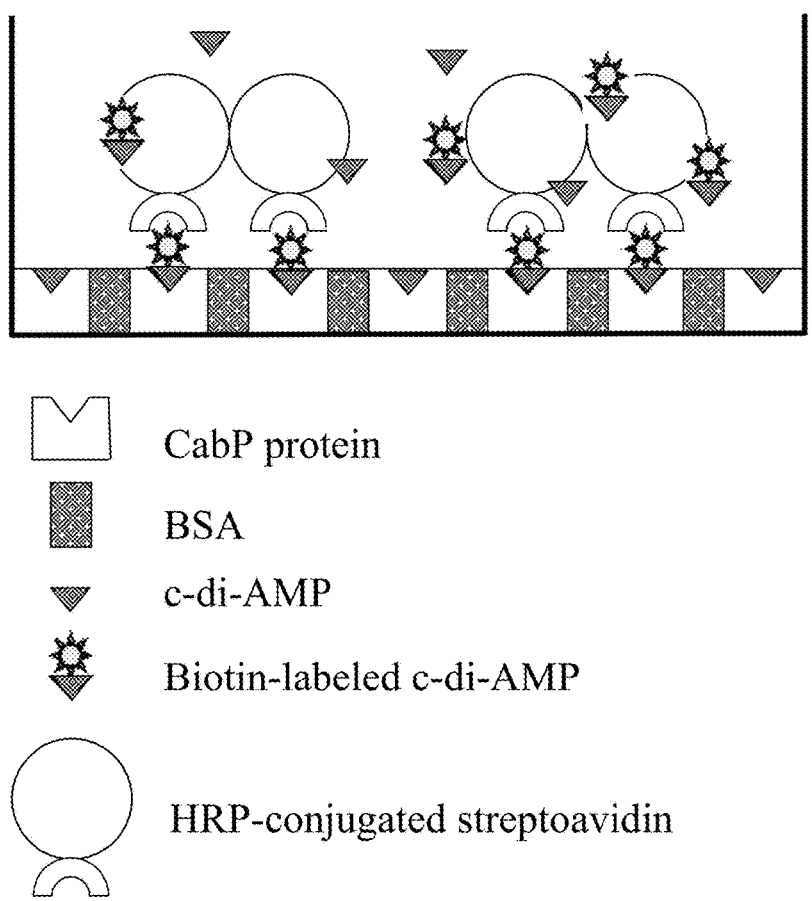
FIG. 4 is a schematic showing an embodiment of a detection method disclosed herein.

In one embodiment, the method employs a basic enzyme-linked immunosorbent assay (ELISA) format as shown in FIG. 4. Components of the assay may include CabP protein, biotinylated c-di-AMP, and a derivatized biotin-binding protein, for example, horseradish peroxidase (HRP)-streptavidin or a similar avidin product. Optionally, assay components include assay buffers, standardized preparations of c-di-AMP and the like.

In one embodiment, the method relies on a biotin-(strept) avidin system as part of the detection mechanism, using a biotinylated competitor and an enzyme-conjugated biotin-binding protein having a chromogenic or fluorgenic substrate to generate a detectable signal.

In one embodiment, biotin-c-di-AMP is used as the competitor. Biotinylation strategies are well known in the art and biotinylation reagents are widely available; these are extremely easy to use by following well-established procedures available in the literature and from the reagent manufacturers. Additionally, derivatized biotin-binding proteins such as avidin and streptavidin (e.g., with fluorophores, enzymes, metals, proteins, solid supports) are readily available.

In one embodiment, a solid support (for example a 96-well plate) is coated with CabP protein; then, the support is blocked with a 1% BSA solution for about 1 hour. c-di-AMP-containing samples are mixed with biotin-labeled c-di-AMP, contacted with the CabP-coated solid support and incubated for a time sufficient for the components of the assay to react and reach equilibrium. In one embodiment, the reaction mixture is incubated for a period of from about 1 to about 3 hours. In one embodiment, an incubation period of about 2 hours is used.

At the end of the incubation period, the solid support is washed thoroughly and enzyme-conjugated biotin-binding protein (e.g. HRP-streptavidin) is added and the mixture incubated for a period of about 30 minutes to 2 hours. The solid support is again washed and enzyme substrate added. Finally, the absorbance of the samples is read. The amount of labeled c-di-AMP is extrapolated from a standard curve and the amount of unlabeled c-di-AMP in the sample indirectly correlates with the amount of signal generated in the sample.

In one embodiment, a microtiter plate is used as the solid support. Following the process steps outlined above, the samples can be read with an absorbance microplate reader.

c-Di-AMP Binding Protein (CabP)

The present c-di-AMP detection/quantification assay is based on the specific binding of c-di-AMP to a c-di-AMP binding protein, CabP.

In one embodiment, a c-di-AMP binding protein useful for the specific detection of c-di-AMP has the amino acid sequence of SEQ ID NO: 1 In one embodiment, the CabP includes a histidine tag containing from 1-6 histidine residues. An example of an amino acid sequence of a CabP with a six residue-His tag is shown in SEQ ID NO: 7.

Expression of Recombinant CabP

Expression of a recombinant CabP for practicing the method of the invention can be achieved using well-established recombinant techniques. In one embodiment, expression of a full-length CabP was obtained by PCR amplification of the open reading frame of S. pneumoniae CabP and cloning into a pET28a(+) plasmid. The recombinant plasmid, designated pST2788, was transformed and maintained in E. coli BL21(DE3) as the expression strain to produce N-His-tagged CabP. The nucleotide sequence of pST2788 containing the sequence for S. pneumoniae CabP is given in SEQ ID NO: 2.

Colonies of the expression strain were grown, selected for, production of CabP induced, and the bacteria harvested. The Cab was isolated and purified, the concentration of purified protein determined and the protein was aliquoted and stored for later use.

Kits

Kits containing the reagents for practicing the c-di-AMP detection method disclosed are encompassed by the invention. A kit in accordance with the invention comprises the following: (a) a c-di-AMP binding protein; (b) biotin-labeled c-di-AMP; (c) enzyme-conjugated biotin-binding protein; and (d) enzyme substrate. Optionally, the kits further include buffers and standard preparations of c-di-AMP.

EXAMPLES

Identification of c-Di-AMP Binding Protein in *Streptococcus pneumoniae*

*Streptococcus pneumoniae* D39 derivative ST581 was grown in 50 ml THY overnight at 37° C. with 5% CO2. Bacteria were harvested, and the pellet was resuspended into 10 ml phosphate-buffered saline (PBS) containing 0.5% (v/v) Triton X-100 followed by sonication for 5 min (10 s on and 5 sec off). The bacterial debris was removed by centrifugation at 12,000 rpm at 4° C. for 20 min. The supernatant was collected, filtered with a 0.45 µm filter, and loaded onto a 2'-AHC-c-di-AMP agarose column (Biolog). The column was then washed with 20 ml PBS containing 1% (v/v) Triton X-100 at a flow rate of 1 ml/min. Subsequently, the proteins were eluted from the column with 5 ml of 9 M urea in PBS containing 1% (v/v) Triton X-100. The eluted samples were analyzed by SDS-PAGE. A protein was significantly enriched (FIG. 2), which was identified as SPD_0077 protein by mass spectrometry. We designated this protein CabP for c-di-AMP binding protein.

Expression and Purification of CabP

The open reading frame of S. pneumoniae cabP was amplified by PCR with primers Pr2974, 5'-TTTCATAT-GTCAGATCGTACGATTGG (SEQ ID NO: 3) and Pr2975, TTTAAGCTTACGAATTCAATGCTAC (SEQ ID NO: 4) using S. pneumoniae D39 genomic DNA as template. The PCR product was digested with NdeI and HindIII, cloned into pET28a(+) plasmid (Novagen) between NdeI and HindIII sites, and was sequence verified. This recombinant plasmid was designated pST2788. The plasmid was transformed and maintained in E. coli BL21(DE3) as the expression strain to produce N-His-tagged CabP.

A single colony of the expression strain was picked and grown in (LB) broth containing 25 µg/ml kanamycin overnight as seeds. Five hundred milliliter LB broth containing 25 µg/ml kanamycin was inoculated with 5 ml overnight culture and shaken at 37° C. with aeration until OD600 to 0.6. The production of CabP was induced with 0.1 mM isopropyl β-D-1-thiogalactopyranoside (IPTG) for 3 h at room temperature. Bacteria were harvested and resuspended into 40 ml lysis buffer (50 mM Tris-HCl, pH 7.5, 500 mM NaCl, 10 mM imidazole, and 10% glycerol). The suspension was sonicated for 10 min on ice with 5 s on and 10 sec off. The bacterial debris was removed by centrifugation at 13,000 rpm for 20 min at 4° C. The supernatant was then loaded onto a column with Ni-NTA resin (Qiagen), washed with 50 ml Buffer I (50 mM Tris-HCl, pH 7.5, 500 mM NaCl, and 30 mM imidazole) followed with 50 ml Buffer 11(50 mM Tris-HCl, pH 7.5, 500 mM NaCl, and 50 mM imidazole). The protein was finally eluted with 20 ml elution buffer (50 mM Tris-HCl, pH 7.5, 500 mM NaCl, and 250 mM imidazole) and dialyzed twice with PBS and once with PBS containing 10% (v/v) glycerol. The purity of the purified protein was determined by SDS-PAGE. The concentration of the purified protein was determined with Pierce BCA protein assay kit (Thermo Scientific). The protein was then aliquoted and stored at −80° C. until use.

Verification of c-Di-AMP Binding by CabP

Figure 2A:
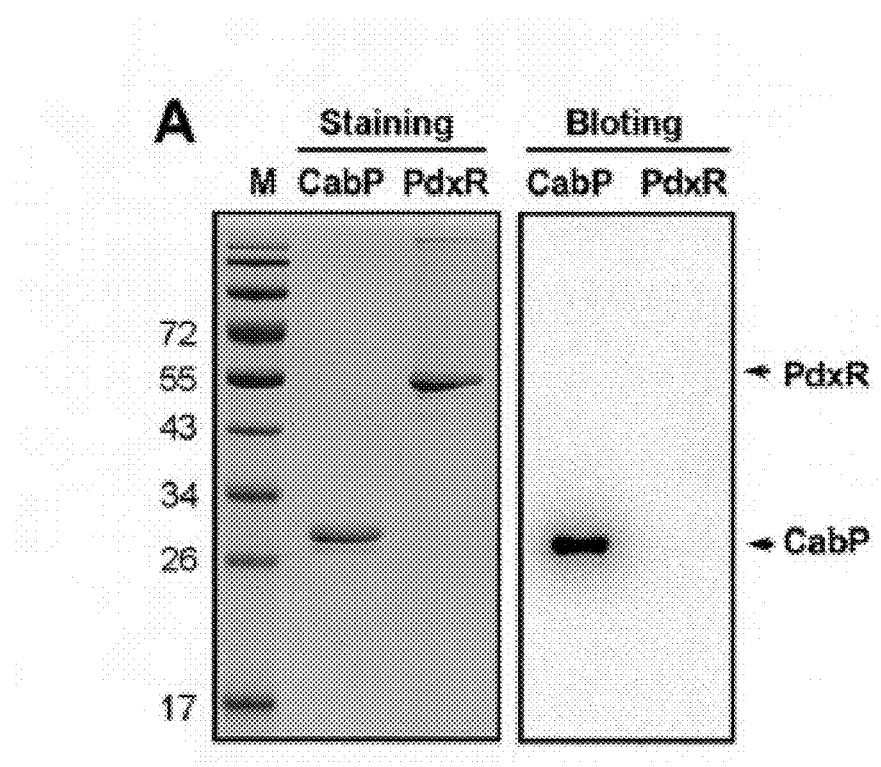
FIGS. 2A-D Interaction of CabP with c-di-AMP. (A) CabP and PdxR (control) were loaded for SDS-PAGE. Gels were either stained with Coomassie Bright Blue (Staining) or blotted with labeled c-di-AMP (Blotting). M, molecular weight marker (Fisher Scientific). (B) Separation of CabP and c-di-AMP reactions with 8% native gel. (C) Mobility of c-di-AMP in the presence or absence of the indicated proteins. (D) Mobility of labeled c-di-AMP mixed with 1 µM CabP in the presence or absence of the indicated unlabeled nucleotides. "cold nt" refers to unlabeled nucleotide.
Figure 2B:
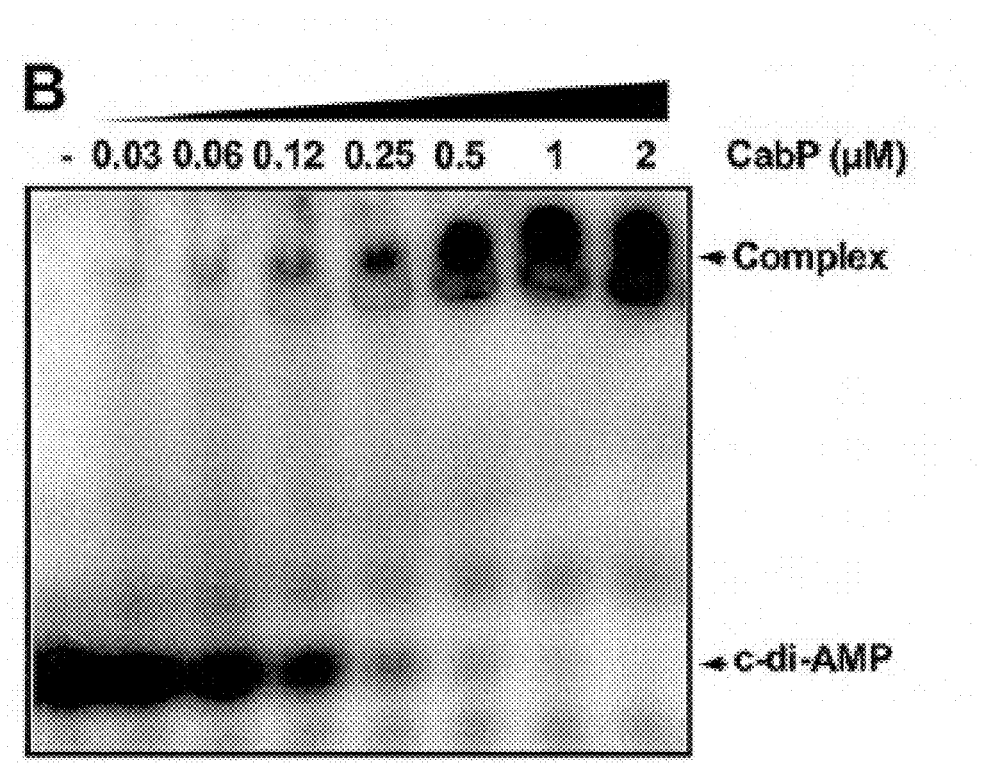
Figure 2C:
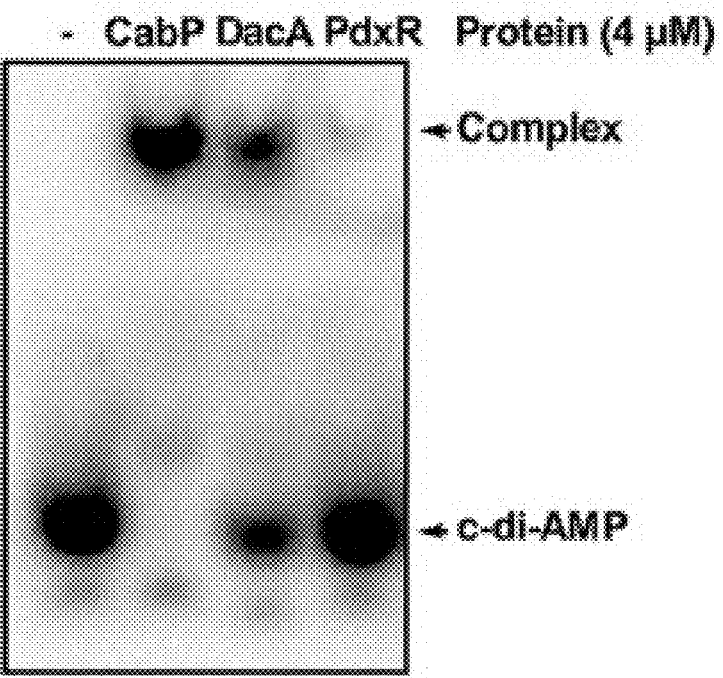
Figure 2D:
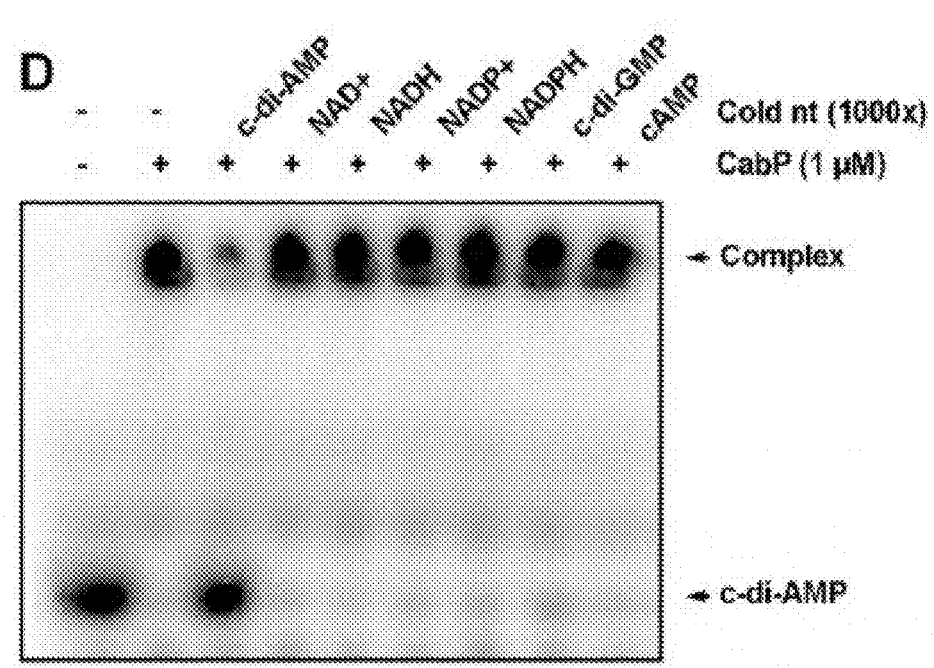
Figure 3:
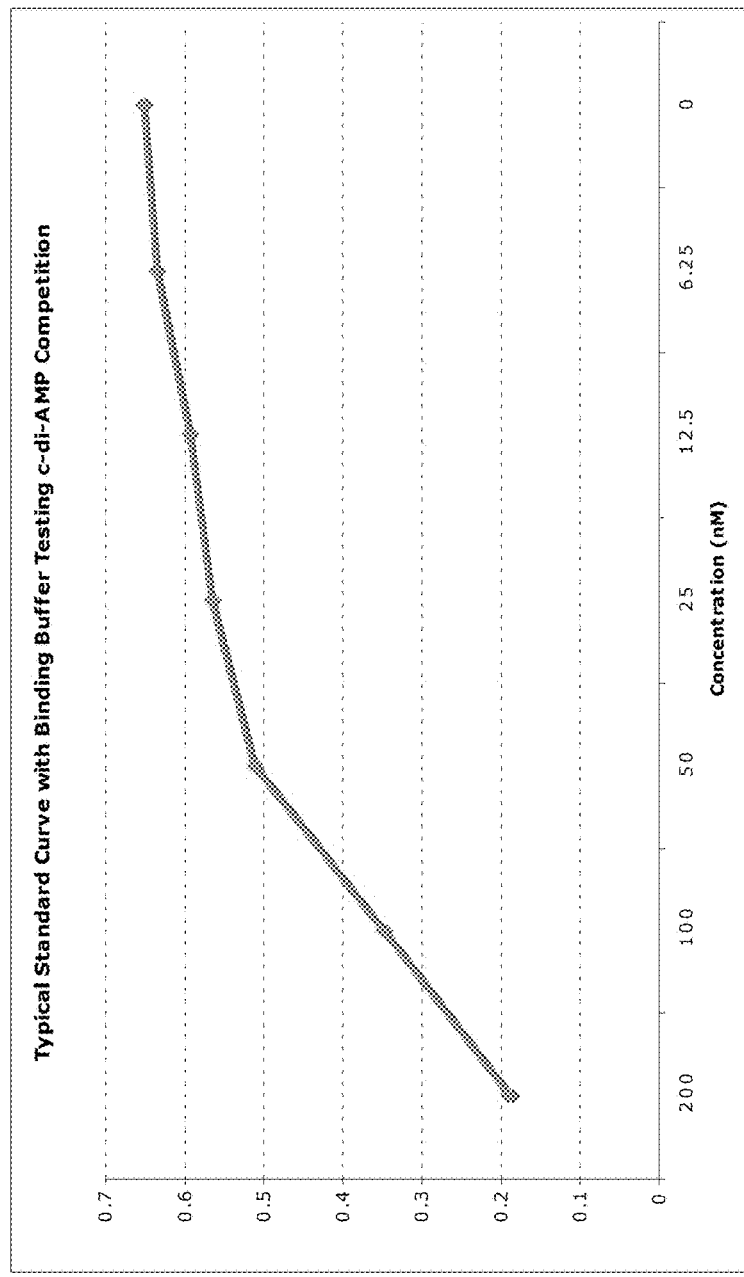
FIG. 3 shows the results of a typical colorimetric standard curve using the given ratio and concentrations of both biotin-labeled c-di-AMP and unlabeled c-di-AMP in binding buffer. Because a 2-fold dilution scheme was used this data can then be plotted using log 2 and a second order polynomial regression fit or linear fit can be utilized to determine sample concentration from any given absorbance reading.

The interaction between CabP and c-di-AMP was evaluated by multiple approaches. First, CabP protein was run along with a control protein, PdxR (1), with duplicate loadings in SDS-PAGE, staining of half the gel indicates that similar amount of proteins were loaded (FIG. 2A). Proteins in the other half gel were transferred onto PVDF membrane and incubated with [α-$^{32}$P]c-di-AMP, which we generated from [α-$^{32}$P]ATP (MP Biomedicals) using purified *Mycobacterium tuberculosis* DacA (2). The result showed that only CabP, but not PdxR, bound with labeled c-di-AMP (FIG. 2A). We then incubate labeled c-di-AMP with various concentration of CabP in the reaction with 50 mM Tris-HCl (pH7.5), 10 mM $MgCl_2$, 5 mM $CaCl_2$, 5 mM KCl, and 10% (v/v) glycerol. The samples were incubated for 30 min at room temperature and then separated the reactions with 8% native PAGE gel (3). The result showed that the mobility of c-di-AMP was retarded in the presence of CabP with an affinity constant of ~150 nM (FIG. 2B). The retardation was also observed with purified *M. tuberculosis* DacA, the ortholog of which in *Bacillus subtilis* has been shown to bind with c-di-AMP (4). However, the mobility of c-di-AMP was not retarded by PdxR (FIG. 2C), indicating the specificity. Additionally, we noticed the free c-di-AMP could be observed from the gel in the presence of 1,000-fold excess of unlabeled c-di-AMP, but not the other nucleotides as indicated (FIG. 2D), indicating that the binding site of c-di-AMP in CabP is very specific to c-di-AMP.

Detection of c-Di-AMP Using Enzyme-Linked Immunosorbent Assay (ELISA) with Purified CabP The binding of c-di-AMP by CabP is very specific with good affinity, therefore, an ELISA method using a solid support coated with CabP to detect c-di-AMP was developed (FIG. 4). The coating concentration of CabP (Table 1) and the concentration of biotin-AHC-c-di-AMP (Table 2) were optimized.

TABLE 1

| Concentr Ab | 50 μg/ml CabP | 50 μg/ml BSA | 10 μg/ml CabP |
|---|---|---|---|
| | 590 | | |
| 100 | 0.9088 | 0.0399 | 1.0408 |
| 50 | 0.7853 | 0.0393 | 0.8881 |
| 25 | 0.712 | 0.0386 | 0.7834 |
| 12.5 | 0.4438 | 0.0388 | 0.5726 |
| 6.25 | 0.2723 | 0.0385 | 0.3835 |
| 3.125 | 0.1654 | 0.0393 | 0.2031 |
| 1.5625 | 0.1044 | 0.0423 | 0.1008 |
| 0.7813 | 0.0904 | 0.059 | 0.0594 |
| 0.3906 | 0.063 | 0.045 | 0.0497 |
| 0.1953 | 0.0591 | 0.0456 | 0.0456 |
| 0.0977 | 0.0526 | 0.0435 | 0.0438 |
| 0.0488 | 0.0505 | 0.0427 | 0.0438 |
| 0.0244 | 0.0479 | 0.0436 | 0.0432 |
| 0.0122 | 0.0518 | 0.0698 | 0.0447 |
| 0.0061 | 0.0542 | 0.0805 | 0.0421 |

TABLE 2

| Binding Buffer [B-c-di-AMP] | |
|---|---|
| 100 | 1.4377 |
| 50 | 1.352 |
| 25 | 1.1813 |
| 12.5 | 0.8821 |
| 6.25 | 0.7071 |
| 3.125 | 0.4685 |
| 1.5625 | 0.2503 |
| 0.78125 | 0.158 |

In one embodiment, a 96-well microtiter plate was coated with CabP at 50 μg/ml in coating buffer (3.03 g/L $Na_2CO_3$ and 6.0 g/L $NaHCO_3$), 100 μl/well, sealed and incubated overnight at 4° C.

The coating solution was removed by washing three times, that is, by filling the wells with 200 μl phosphate buffered saline (PBS) containing 0.05% (v/v) polysorbate 20 (TWEEN®-20), and aspirating.

The wells of the microtiter plate were then blocked with a blocking solution (1% BSA in PBS), 100 μl/well, and the plate incubated 1 h at room temperature.

To remove the blocking solution, the plates were washed 3 times with PBS containing 0.05% (v/v) polysorbate 20 (TWEEN®-20). 25 nM biotin-labeled c-di-AMP was diluted in 50 mM Tris-HCl (pH 8.0) or other appropriate media/solution and mixed with two-fold serial diluted standards (from 200 nM to 6.25 nM), or samples prepared within 50 mM Tris-HCl (pH 8.0) or the same media/solution. 100 μl/well, incubate 2 h at room temperature.

The standards and the samples were removed, and the wells washed 3 times with PBS containing 0.05% (v/v) polysorbate 20 (TWEEN®-20).

Streptavidin-HRP (Thermo Scientific) diluted at 1:10,000 with PBS containing 0.05% (v/v) polysorbate 20 (TWEEN®-20), was added to the wells, 100 μl/well, and the plate incubated 1 h at room temperature.

The streptavidin-HRP solution was removed by washing the wells 3 times with PBS containing 0.05% (v/v) polysorbate 20 (TWEEN®-20).

Figure 5:
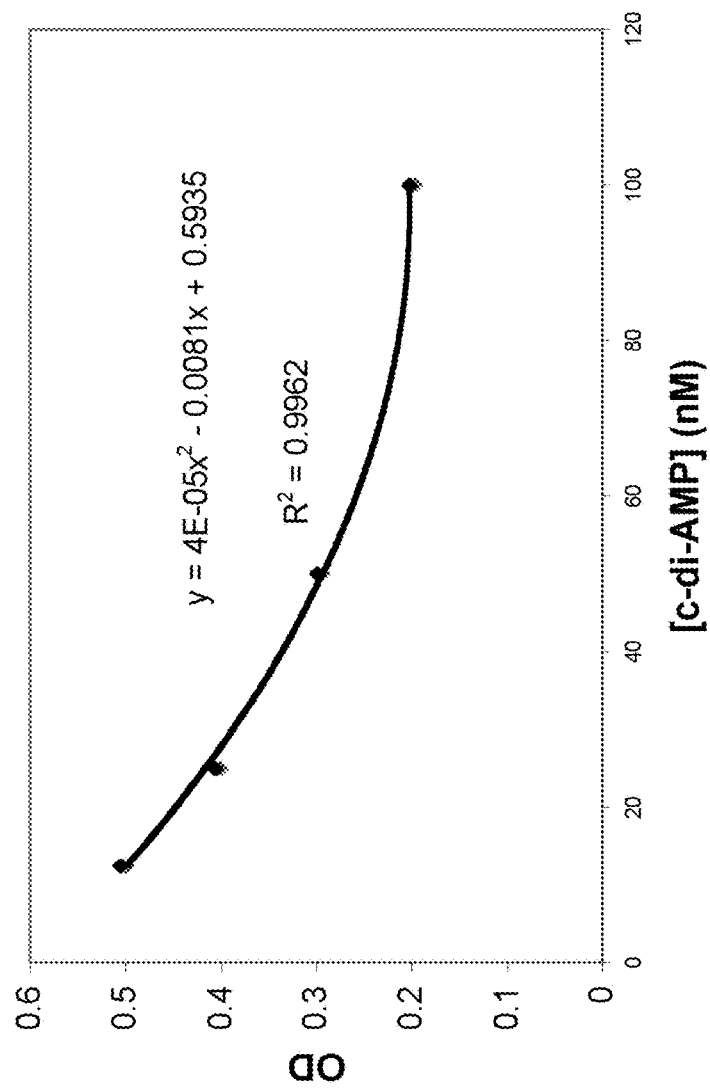
FIG. 5 shows a standard curve for the c-di-AMP ELISA.
Figure 6:
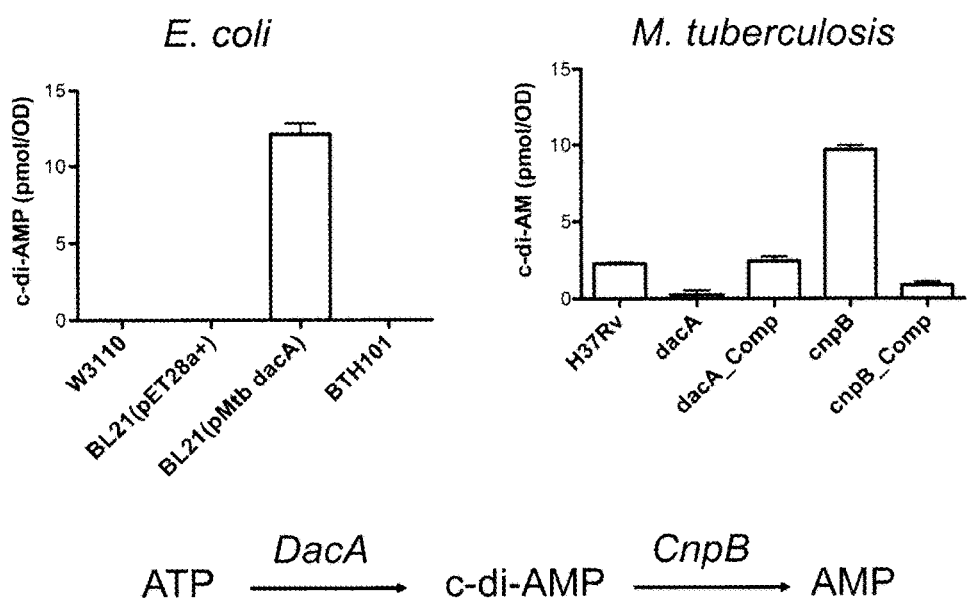
FIG. 6 shows the results of the detection of c-di-AMP in *M. tuberculosis* using the method disclosed. *M. tuberculosis* H37Rv and its derivatives as indicated were grown in Sauton's broth for 7 days. Bacteria were harvested by centrifugation at 5,000 rpm for 10 min at room temperature. One milliliter of supernatant was collected as secreted sample for each strain, and the bacterial pellet was resuspended in 500 µl 50 mM Tris-HCl (pH8.0), heated 1 h at 90° C. and disrupted using a bead-beater (Biospec). The lysates were centrifuged at 13,000 rpm for 10 min and the supernatant was collected as bacterial c-di-AMP sample for each strain. c-di-AMP of both the bacterial and the secreted samples were measured using ELISA that we have developed. Note that for bacterial samples, c-di-AMP standards were diluted in 50 mM Tris-HCl (pH8.0) and for secreted samples, c-di-AMP standards were diluted in Sauton's broth, as suggested in the protocol.
Figure 7A:
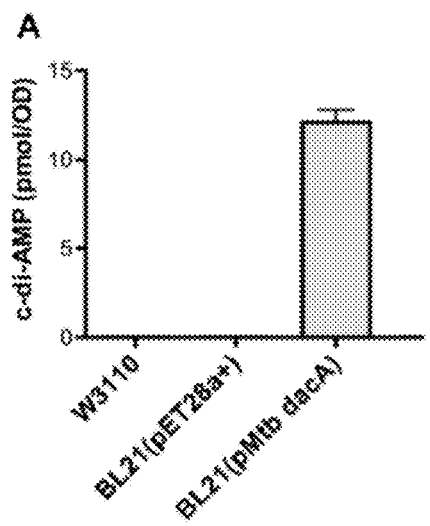
FIG. 7A-B shows the results of the detection of c-di-AMP in *E. coli* (A) and *S. pneumoniae* (B). (A) *E. coli* W3110, expression control strain BL21(pET28a+), and expression strain BL21(pMtb_DacA) that expresses Mtb dacA were grown in LB broth overnight. Bacteria were harvested and resuspended in 0.5 ml 50 mM Tris-HCl. After sonication, the bacterial debri was removed and the supernatant was used to detect c-di-AMP. It is known that *E. coli* does not possess c-di-AMP. However, the strain expressing Mtb dacA produce significant amount of c-di-AMP. (B) *S. pneumoniae* D39 and three c-di-AMP phosphodiesterase mutants were grown in THY broth until the optical density (OD) at 620 nm ($OD_{620}$) to 0.3 and 0.8. Samples were prepared and detected similarly as described in panel A. This result indicates that bacterial c-di-AMP levels are increased in c-di-AMP phosphodiesterase mutants compared to that of the WT.
Figure 7B:
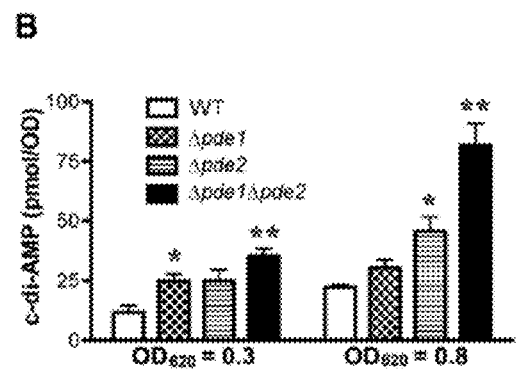

A substrate solution [20 ml 0.1 M citric acid (pH 5.0), 20 μl 30% $H_2O_2$, and 10 mg o-phenylenediamine (OPD) (Sigma, 1 tablet)], 100 μl/well, was added to each well. After approximately 30 minutes (typical) or sufficient color development, 100 μl/well stop solution (2 N $H_2SO_4$) was added to each well. The absorbance of each well was read with a plate reader at 492 nm.

c-di-AMP concentration was calculated based on the standard curve shown in FIG. 5.

Truncation of CabP

To investigate the c-di-AMP binding region of CabP, truncated forms of CabP were expressed and their ability to bind c-di-AMP examined.

The following diagram shows the location of NAD binding, TrkA_N and TrkA_C domains of full length CabP. Truncated forms included: P1, in which 15 amino acids were removed from the N-terminal of CabP; P2, which results from the removal of 94 amino acid residues from the C-terminal of CabP, thereby eliminating the TrkA_C region; and P3, in which both N- and C-terminal ends of CabP are truncated.

|          | NAD binding | TrkA_N | TrkA_C |
|----------|-------------|--------|--------|
| pST2788  | ─────────────────────────────────── |
| P1       | 15 aa ─────────────────────── |
| P2       | ──────────────── 94 aa |
| P3       | ──────────── |

All PCR products were cloned into pET28a(+) to express P1, P2, and P3. These proteins were then used to evaluate their interaction with c-di-AMP.

1. Expression of full-length CabP from pST2788 (the nucleotide sequence of the pST2788 plasmid is given in SEQ ID NO: 2)

```
Pr2974
                                          (SEQ ID NO: 3)
(5'-TTTCATATGTCAGATCGTACGATTGG)

Pr2975
                                          (SEQ ID NO: 4)
(TTTAAGCTTACGAATTCAATGCTAC)
```

2. Expression of CabP P1 (NdeI+HindIII) 633 bp (Remove 15 aa)

```
Pr3061
                                          (SEQ ID NO: 5)
tttcatatgagcagtgtcctagctgccc Pr2975
                                          (SEQ ID NO: 4)
(TTTAAGCTTACGAATTCAATGCTAC)
```

3. Expression of cabP P2 (NdeI+HindIII) 395 bp (Remove 94 aa)

```
Pr2974
                                          (SEQ ID NO: 3)
(5'-TTTCATATGTCAGATCGTACGATTGG)

Pr3062
                                          (SEQ ID NO: 6)
tttaagcttactgccccatttcatactctgg
```

4. Expression of cabP P3 (NdeI+HindIII) 3356 bp

```
Pr3061
                                          (SEQ ID NO: 5)
tttcatatgagcagtgtcctagctgccc Pr3062
                                          (SEQ ID NO: 6)
tttaagcttactgccccatttcatactctgg
```

No binding of P1, P2 or P3 was observed using biotin-labeled c-di-AMP, while binding to intact CabP expressed from pST2788 was normal.

While no clear conclusions can be drawn from this data, it may suggest that the binding domain on CabP for c-di-AMP is a conformational one rather than a linear one such that alteration of the full length CabP affects its conformation sufficiently to interfere with binding of c-di-AMP, or that biotin-labeled c-di-AMP differs from unlabeled c-di-AMP in its interaction with CabP. Therefore, the genus of CabPs that will function in the disclosed assay is not necessarily coextensive with all proteins which are capable of binding to c-di-AMP.

---

I claim:

1. A method for the detection of cyclic di-adenosine monophosphate (c-di-AMP), the method comprising:
   (a) contacting a sample with a specific c-di-AMP binding protein (CabP) in the presence of biotin-labeled c-di-AMP for a time sufficient for binding of c-di-AMP and biotin-labeled c-di-AMP in the sample to reach equilibrium;
   (b) contacting said sample with an enzyme-conjugated biotin-binding protein that binds the biotin-labeled c-di-AMP in said sample;
   (c) contacting said sample with a chromogenic substrate for the enzyme for a time sufficient for oxidation of the substrate to yield a detectable signal; and
   (d) measuring the detectable signal, wherein said signal correlates to the amount of unlabeled c-di-AMP in said sample.

2. The method of claim 1, wherein said CabP has the amino acid sequence of SEQ ID NO: 1.

3. The method of claim 1, wherein said CabP has the amino acid sequence of SEQ ID NO: 7.

4. The method of claim 1, wherein said enzyme-conjugated biotin-binding protein is horseradish peroxidase (HRP)-streptavidin.

5. The method of claim 1, wherein said contacting step (a) is for a time sufficient for binding of labeled and unlabeled c-di-AMP to CabP to achieve equilibrium.

6. The method of claim 1, wherein said contacting step (a) is for from about 1 to about 3 hours.

7. The method of claim 1, wherein said contacting step (a) is for about 2 hours.

* * * * *